US012133629B2

(12) United States Patent
Powell et al.

(10) Patent No.: US 12,133,629 B2
(45) Date of Patent: Nov. 5, 2024

(54) MEDICAL DEVICE ACTUATORS

(71) Applicant: Boston Scientific Scimed, Inc., Maple Grove, MN (US)

(72) Inventors: Sean Powell, Holden, MA (US); Matthew Jagelski, Marlborough, MA (US); Michael McBrien, Jamaica Plain, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 102 days.

(21) Appl. No.: 17/562,418

(22) Filed: Dec. 27, 2021

(65) Prior Publication Data

US 2022/0202280 A1  Jun. 30, 2022

Related U.S. Application Data

(60) Provisional application No. 63/132,538, filed on Dec. 31, 2020.

(51) Int. Cl.
  *A61B 1/00* (2006.01)
  *A61B 1/005* (2006.01)
  *A61B 1/008* (2006.01)
(52) U.S. Cl.
  CPC ........ *A61B 1/00098* (2013.01); *A61B 1/0057* (2013.01); *A61B 1/008* (2013.01)
(58) Field of Classification Search
  CPC ... A61B 1/00098; A61B 1/0057; A61B 1/008; A61B 1/0052
  See application file for complete search history.

(56) References Cited

U.S. PATENT DOCUMENTS

| 8,753,263 B2 | 6/2014 | Arai |
| 10,357,145 B2 | 7/2019 | Fukushima et al. |

(Continued)

FOREIGN PATENT DOCUMENTS

| JP | 2017213061 | 12/2017 |
| WO | 2021249601 A1 | 12/2021 |

OTHER PUBLICATIONS

International Search Report and Written Opinion issued in International Application No. PCT/US2021/065202, issued Mar. 31, 2022 (38 pages).

*Primary Examiner* — Anh Tuan T Nguyen
*Assistant Examiner* — Rynae E Boler
(74) *Attorney, Agent, or Firm* — Bookoff McAndrews, PLLC

(57) ABSTRACT

A linkage assembly for a medical device may comprise: a rotatable member configured to rotate about a rotation axis; a piston; and a connecting rod rotatably connected to the rotatable member and the piston and movable along a range. A first end of the range may correspond to an initial position of a distal member movable by the linkage assembly, and a second end of the range may correspond to a final position of a distal member. In a first configuration of the connecting rod, at the first end of the range, a proximal end of the connecting rod may be offset from a longitudinal axis by a first amount, wherein the longitudinal axis is perpendicular to the rotation axis; In a second configuration of the connecting rod, at the second end of the range, the proximal end of the connecting rod may be offset from the longitudinal axis by a second amount. The second amount may be less than two-thirds of the first amount.

20 Claims, 9 Drawing Sheets

(56) References Cited

U.S. PATENT DOCUMENTS

| | | | |
|---|---|---|---|
| 2002/0091303 A1* | 7/2002 | Ootawara | A61B 1/01 600/106 |
| 2003/0073955 A1* | 4/2003 | Otawara | A61B 1/00098 600/101 |
| 2015/0148598 A1* | 5/2015 | Fukushima | A61B 1/0052 600/109 |
| 2016/0089003 A1 | 3/2016 | Morimoto et al. | |
| 2016/0089125 A1* | 3/2016 | Morimoto | A61B 1/00098 600/107 |
| 2017/0000316 A1* | 1/2017 | Sueyasu | A61B 1/00 |
| 2020/0146534 A1 | 5/2020 | Harada | |

* cited by examiner

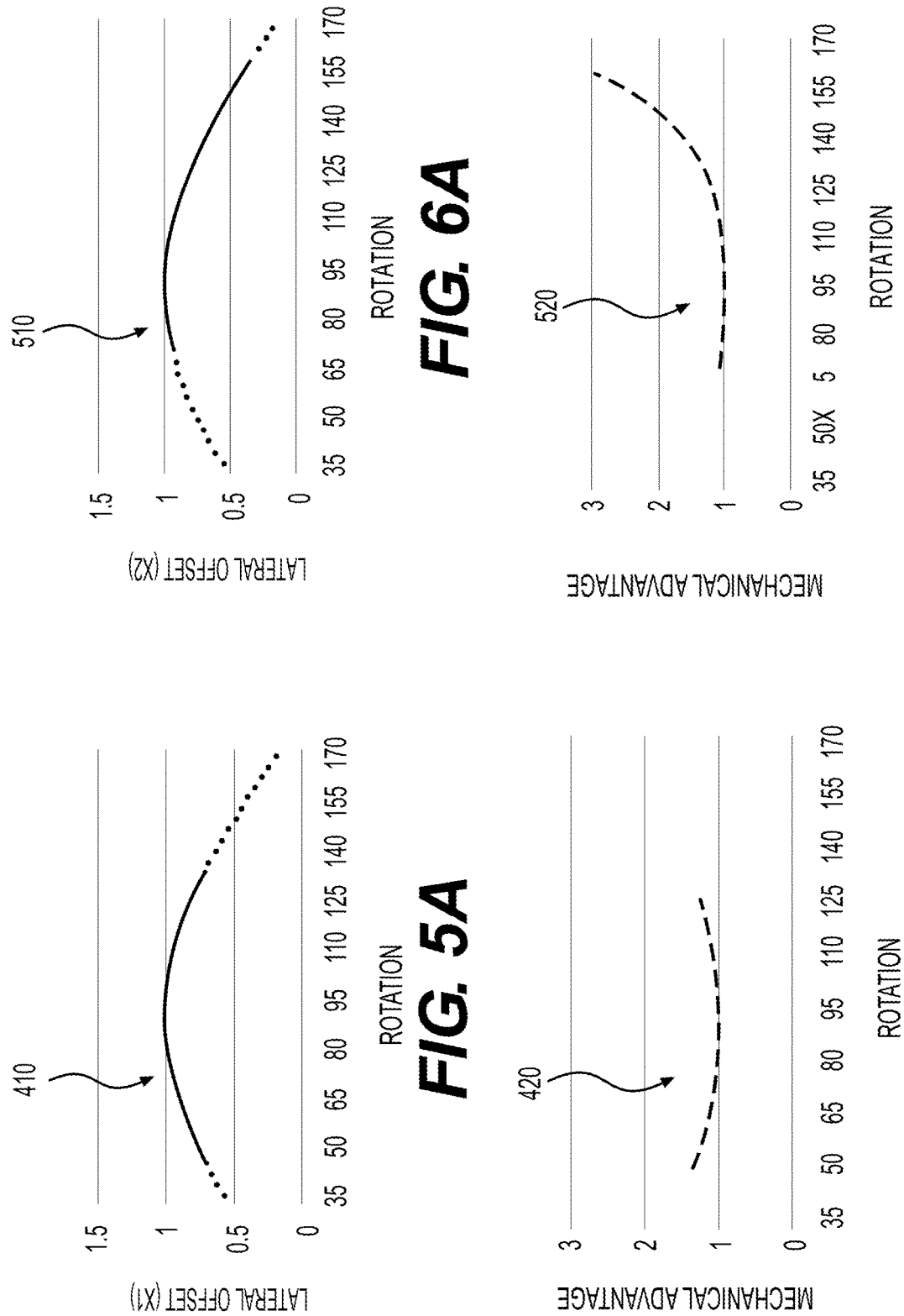

MEDICAL DEVICE ACTUATORS

CROSS-REFERENCE TO RELATED APPLICATIONS

This patent application claims the benefit under 35 U.S.C. § 119 to U.S. Provisional Patent Application No. 63/132,538, filed on Dec. 31, 2020, the entirety of which is incorporated herein by reference.

TECHNICAL FIELD

Various aspects of this disclosure relate generally to devices and methods for actuators of medical devices, and in particular to actuators for components of duodenoscopes, such as elevator levers.

BACKGROUND

Duodenoscopes may include a handle and a sheath insertable into a body lumen of a subject. The sheath may terminate in a distal tip portion, which may include features such as optical elements (e.g., camera, lighting), air/water outlets, and working channel openings. An elevator may be disposed at a distal tip and may be actuatable in order to change an orientation of a medical device/tool passed through the working channel. For example, the elevator may be pivotable or otherwise movable.

Elements/actuators in the handle may control the elements of the distal tip. For example, buttons, knobs, levers, etc. may control elements of the distal tip. The elevator may be controlled via a control mechanism in a handle, such as a lever, which may be attached to a control wire that attaches to the elevator. When a mechanism (e.g., a lever) is actuated, the wire may move proximally and/or distally, thereby raising and/or lowering the elevator.

SUMMARY

Each of the aspects disclosed herein may include one or more of the features described in connection with any of the other disclosed aspects.

In one example, a linkage assembly for a medical device may comprise: a rotatable member configured to rotate about a rotation axis; a piston; and a connecting rod rotatably connected to the rotatable member and the piston and movable along a range. A first end of the range may correspond to an initial position of a distal member movable by the linkage assembly, and a second end of the range may correspond to a final position of a distal member. In a first configuration of the connecting rod, at the first end of the range, a proximal end of the connecting rod may be offset from a longitudinal axis by a first amount, wherein the longitudinal axis is perpendicular to the rotation axis. In a second configuration of the connecting rod, at the second end of the range, the proximal end of the connecting rod may be offset from the longitudinal axis by a second amount. The second amount may be less than two-thirds of the first amount.

Any of the linkage assemblies disclosed herein may have any of the following features. A mechanical advantage of the linkage assembly may be at least 50 percent higher in the second configuration than in the first configuration. The first configuration may be at a starting point of a stroke of the linkage assembly. The second configuration may be at an ending point of the stroke of the linkage assembly. The rotatable member may be rotatable by a lever fixed to the rotatable member. The piston may be operative to move a control wire coupled to the distal member. The distal member may be an elevator of the medical device. In the first configuration, the elevator may be in a fully lowered configuration. In the second configuration, the elevator may be in a fully raised configuration. The connecting rod may not be straight. The connecting rod may have a first segment and a second segment transverse to the first segment. The connecting rod may further have a third segment transverse to the second segment and the first segment. The longitudinal axis may be coaxial with a diameter of the rotatable member that extends through the rotation axis. The longitudinal axis may be approximately parallel to or coaxial with a longitudinal axis defining the movement of the plunger. In the first configuration, the proximal end of the lever may offset, in a first direction, from the longitudinal axis by a first angle. In the second configuration, the proximal end of the lever may be offset, in the first direction, from the longitudinal axis by a second angle. The second angle may be larger than the first angle. The first angle and the second angle each may have a vertex at an intersection of the rotation axis and the longitudinal axis. A first leg of each of the first and the second angle may be defined by a line extending between the rotation axis and the proximal end of the lever. A second leg of each of the first and second angle may be defined by the longitudinal axis.

In another example, a linkage assembly may comprise: a rotatable member configured to rotate about a rotational axis; a piston; and a connecting rod rotatably connected to the rotatable member and the piston and movable along a range. A first end of the range may correspond to an initial position of a distal member movable by the linkage assembly. A second end of the range may correspond to a final position of a distal member. In a first configuration of the connecting rod, at a first end of the range, the linkage assembly may have a first mechanical advantage. In a second configuration of the connecting rod, at a second end of the range, the linkage assembly may have a second mechanical advantage. The second mechanical advantage may be at least 50 percent higher than the first mechanical advantage.

Any of the linkage assemblies disclosed herein may have any of the following properties. In the first configuration, the proximal end of the lever may be offset, in a first direction, from the longitudinal axis by a first angle. In the second configuration, the proximal end of the lever may be offset, in the first direction, from the longitudinal axis by a second angle. The second angle may be larger than the first angle. The first angle and the second angle each may have a vertex at the intersection of the rotation axis and the longitudinal axis. The distal member may be an elevator of the medical device. In the first configuration, the elevator may have a lower deflection angle than in the second configuration.

In another example, a linkage assembly for a medical device may comprise: a connecting rod connected to (a) the rotatable member, configured to rotate about a rotation axis along a range. A first end of the range may correspond to an initial position of a distal member movable by the linkage assembly, and a second end of the range may correspond to a final position of a distal member. The connecting rod may also be connected to (b) a piston. In a first configuration of the connecting rod, in which the connecting rod is positioned at the first end of the range, a proximal end of the connecting rod may be offset from a longitudinal axis, perpendicular to the rotation axis and extending through the rotation axis, by a first amount. In a second configuration of the linkage assembly, in which the connecting rod is positioned at the second end of the range, the proximal end of the connecting rod may be offset form the longitudinal axis by a second amount. The second amount may be less than two-thirds of the first amount. A mechanical advantage of the linkage assembly may be at least 50% higher in the second configuration than in the first configuration.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "diameter" may refer to a width where an element is not circular. The term "distal" refers to a direction away from an operator, and the term "proximal" refers to a direction toward an operator. The term "exemplary" is used in the sense of "example," rather than "ideal." The term "approximately," or like terms (e.g., "substantially"), includes values +/−10% of a stated value.

BRIEF DESCRIPTION OF THE DRAWINGS

The accompanying drawings, which are incorporated in and constitute a part of this specification, illustrate aspects this disclosure and together with the description, serve to explain the principles of the disclosure.

FIGS. 5A-5B are graphs depicting aspects of the lever of FIGS. 2A-2B.

FIGS. 6A-6B are graphs depicting aspects of the levers of FIGS. 3A-4B.

DETAILED DESCRIPTION

Figure 1A:
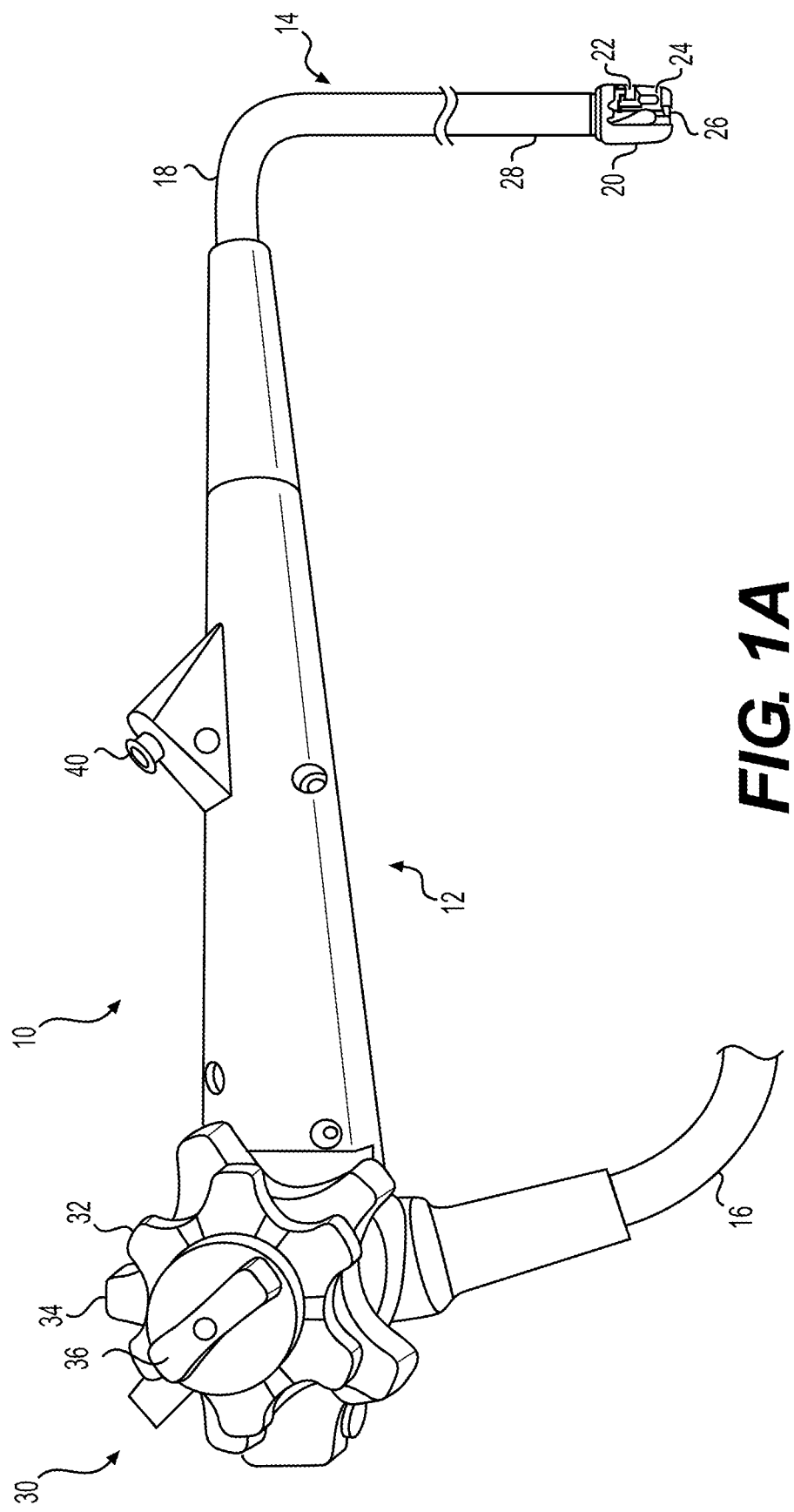
FIGS. 1A and 1B depict aspects of an exemplary duodenoscope.

Actuators of a medical device, for example levers of duodenoscopes, may, in some configurations, require an operator to exert a large amount of force to operate the actuator/lever. For example, levers may be used to raise and/or lower elevators of distal tips of duodenoscopes. During a procedure, an operator may use the lever while a medical device is inserted in a working channel of a duodenoscope in order to change an angle at which the medical device emerges from a distal end of the working channel. The operator may desire to fine-steer the elevator using the lever, in order to provide a precise positioning of the inserted medical device. Fine-steering may be of interest to the operator at angles of the elevator exceeding a particular angle (e.g., 60 degrees). Prior to reaching that particular angle (e.g., 60 degrees), the operator may not be concerned with fine steering the elevator because a final position below that angle is not desired.

An amount of force necessary to bend an elastic member, such as a flexible device/shaft being held by an elevator, generally increases corresponding to the angle of deflection. When raising an elevator carrying a flexible device/shaft, an amount of force to raise the elevator by a given angular increment may increase as the elevator is raised. For example, raising an elevator from 60 to 70 degrees may require more force than raising the elevator from 50 degrees to 60 degrees. Such increased forces may coincide with the raising/bending angle(s) of interest to an operator, described above (e.g., angles above 60 degrees). Articulation of the distal tip of the endoscope may result in a tortuous path for a control wire of the elevators, increasing the amount of force required to raise the elevator in all ranges of the lever, overall (e.g., in the entire range of the lever).

Therefore, it may be desirable to decrease the amount of force required to raise and/or lower the elevator in order to enable an operator to perform a medical procedure. It may be particularly desirable to decrease the amount of force required to raise the elevator at angles of interest (e.g., angles above 60 degrees). Decreased force may facilitate fine steering of the elevator in order to raise a medical tool (inserted in the scope and carried by the elevator) by a particular, desired amount. Furthermore, it may be desirable to increase a velocity of the elevator at lower angles (e.g., angles below 60 degrees) in order to facilitate quickly moving the elevator to the angular range of interest. It may be desirable for the elevator to move with a lower velocity within the range of interest (e.g., above 60 degrees) in order to facilitate fine tuning of the elevator's position.

As described in further detail below, an elevator lever assembly may include a rotatable member having a contact portion for being contacted by a user, a connecting rod rotatably coupled to the rotatable member, and a plunger rotatably coupled to the connecting rod. The components of the lever assembly may be chosen so that a lateral offset of a proximal end of the lever provides a mechanical advantage at higher angles of the elevator's motion. The lateral offset may be in a direction perpendicular to a longitudinal axis of the duodenoscope handle or a longitudinal axis of components of the duodenoscope handle, (e.g., a longitudinal axis coaxial with a central axis of the plunger, or a longitudinal axis coaxial with a center of the rotatable member). The lateral offset at relevant portions of the range of the contact portion (and thus relative portions of the range of the elevator) provides a mechanical advantage at higher angles of the elevator's motion. The mechanical advantage may result in less force being required to raise the elevator at higher angles.

Although the term duodenoscope may be used herein, it will be appreciated that other devices, including, but not limited to, endoscopes, colonoscopes, ureteroscopes, bronchoscopes, laparoscopes, sheaths, catheters, or any other suitable delivery device or medical device that may include an elevator or any other distal component requiring actuation or movement, may be used in connection with the devices and manufacturing methods of this disclosure. Although side-facing devices are particularly discussed, the embodiments described herein may also be used with front-facing endoscopes (e.g., endoscopes where a viewing element faces longitudinally forward). Although the lever assemblies described below are described as being used to raise/lower an elevator, it will be appreciated that the lever assemblies may also be used to control other medical device components (e.g., steering or braking components).

Figure 1B:
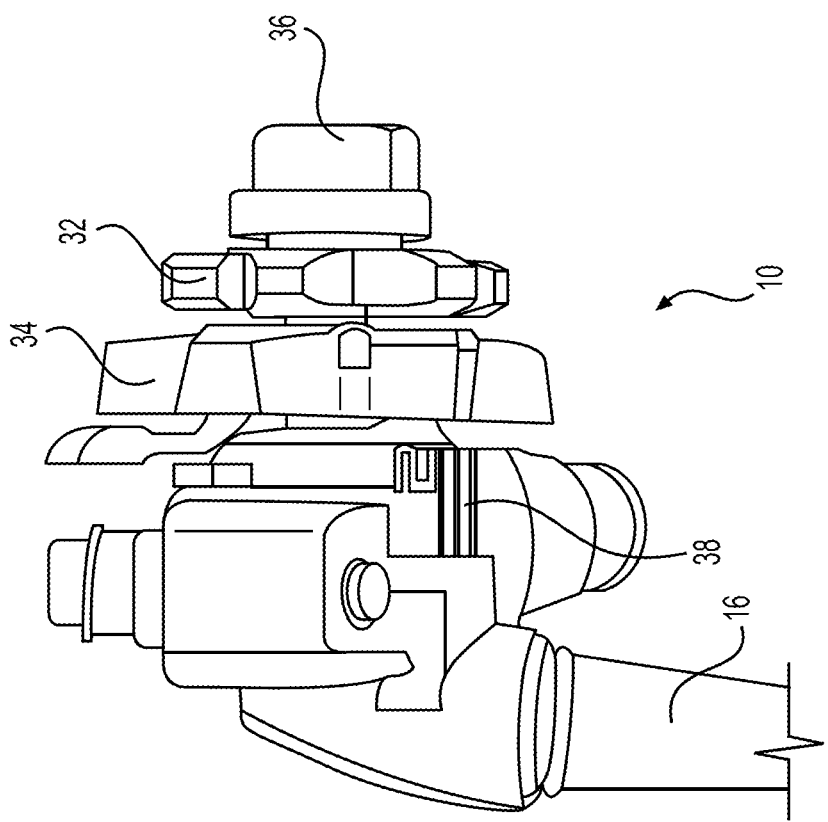

FIG. 1A depicts an exemplary duodenoscope 10 having a handle 12 and an insertion portion 14. FIG. 1B shows a proximal end of handle 12. Duodenoscope 10 may also include an umbilicus 16 for purposes of connecting duodenoscope 10 to sources of, for example, air, water, suction, power, etc., as well as to image processing and/or viewing equipment.

Insertion portion 14 may include a sheath or shaft 18 and a distal tip 20. Distal tip 20 may include an imaging device 22 (e.g., a camera) and a lighting source 24 (e.g., an LED or an optical fiber). Distal tip 20 may be side-facing. That is, imaging device 22 and lighting source 24 may face radially outward, perpendicularly, approximately perpendicularly, or otherwise transverse to a longitudinal axis of shaft 18 and distal tip 20.

Distal tip 20 may also include an elevator 26 for changing an orientation of a tool inserted in a working channel of duodenoscope 10. Elevator 26 may alternatively be referred to as a swing stand, pivot stand, raising base, or any suitable other term. Elevator 26 may be pivotable via, e.g., an actuation wire or another control element that extends from handle 12, through shaft 18, to elevator 26.

A distal portion of shaft 18 that is connected to distal tip 20 may have a steerable section 28. Steerable section 28 may be, for example, an articulation joint. Shaft 18 and steerable section 28 may include a variety of structures which are known or may become known in the art.

Handle 12 may have one or more actuators/control mechanisms 30. Control mechanisms 30 may provide control over steerable section 28 or may allow for provision of air, water, suction, etc. For example, handle 12 may include control knobs 32, 34 for left, right, up, and/or down control of steerable section 28. For example, one of knobs 32, 34 may provide left/right control of steerable section 28, and the other of knobs 32, 34 may provide up/down control of steerable section 28. Handle 12 may further include one or more locking mechanisms 36 (e.g., knobs or levers) for preventing steering of steerable section 28 in at least one of an up, down, left, or right direction. Handle 12 may include an elevator control lever 38 (FIG. 1B). Elevator control lever 38 may raise and/or lower elevator 26, via connection between lever 38 and a wire.

FIGS. 2A-4B depict exemplary connections/linkages between lever 38 and the wire (not shown in the figures) that extends from lever 38, through shaft 18, to elevator 26. A port 40 may allow passage of a tool through port 40, into a working channel of the duodenoscope 10, through sheath 18, to distal tip 20.

In use, an operator may insert at least a portion of shaft 18 into a body lumen of a subject. Distal tip 20 may be navigated to a procedure site in the body lumen. The operator may insert a tool (not shown) into port 40, and pass the tool through shaft 18 via a working channel to distal tip 20. The tool may exit the working channel at distal tip 20. The user may use elevator control lever 38 to raise elevator 26 and angle the tool toward a desired location (e.g., a papilla of the pancreatico-biliary tract). The user may use the tool to perform a medical procedure.

FIGS. 2A-4B depict exemplary linkage assemblies for use with duodenoscope 10. The linkage assemblies of FIGS. 2A-4B may provide functionality to elevator control lever 38 of FIG. 1B, providing linkages for connecting control lever 38 to a wire for deflecting the elevator.

Figure 2A:
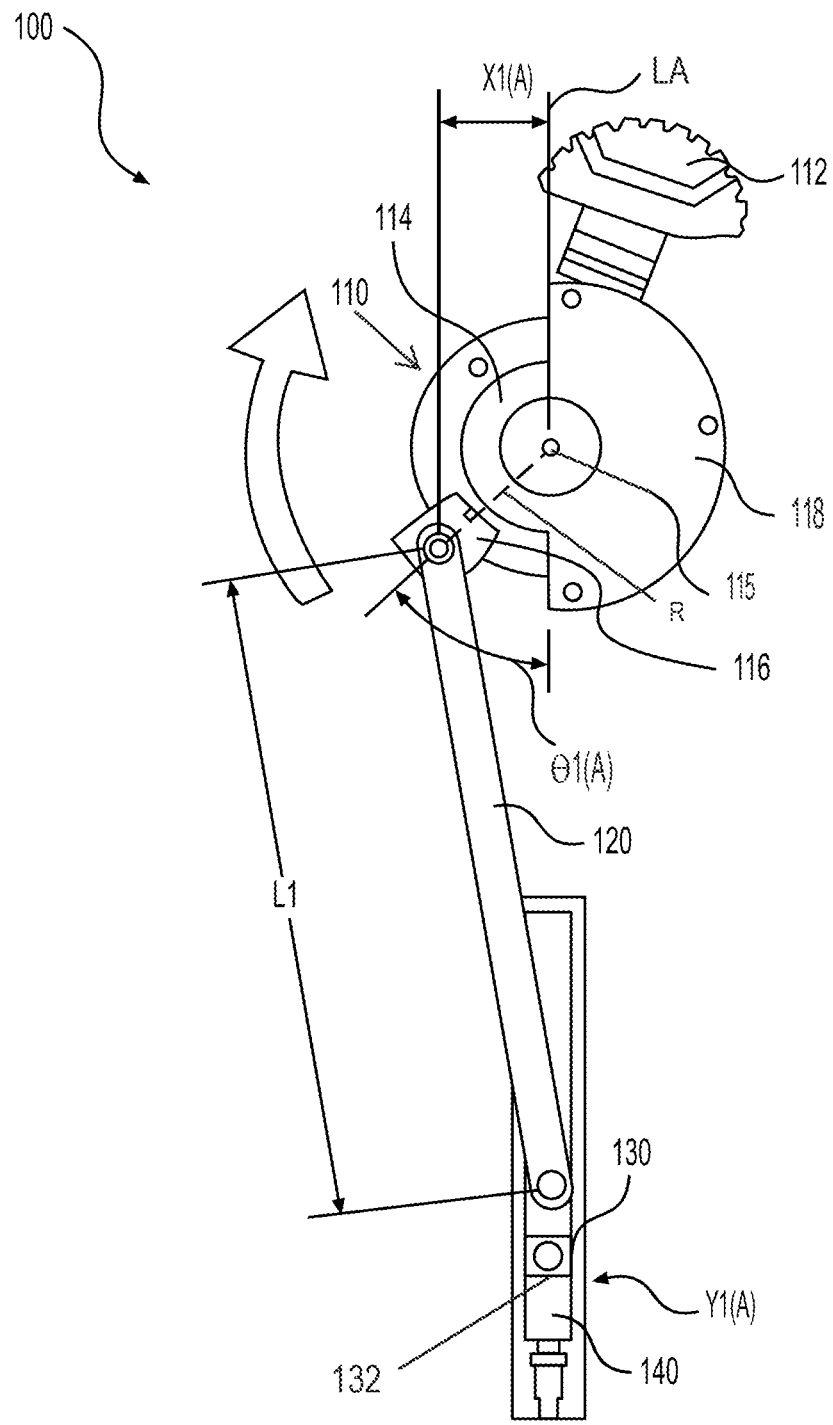
FIGS. 2A-4B depict exemplary lever assemblies.
Figure 2B:
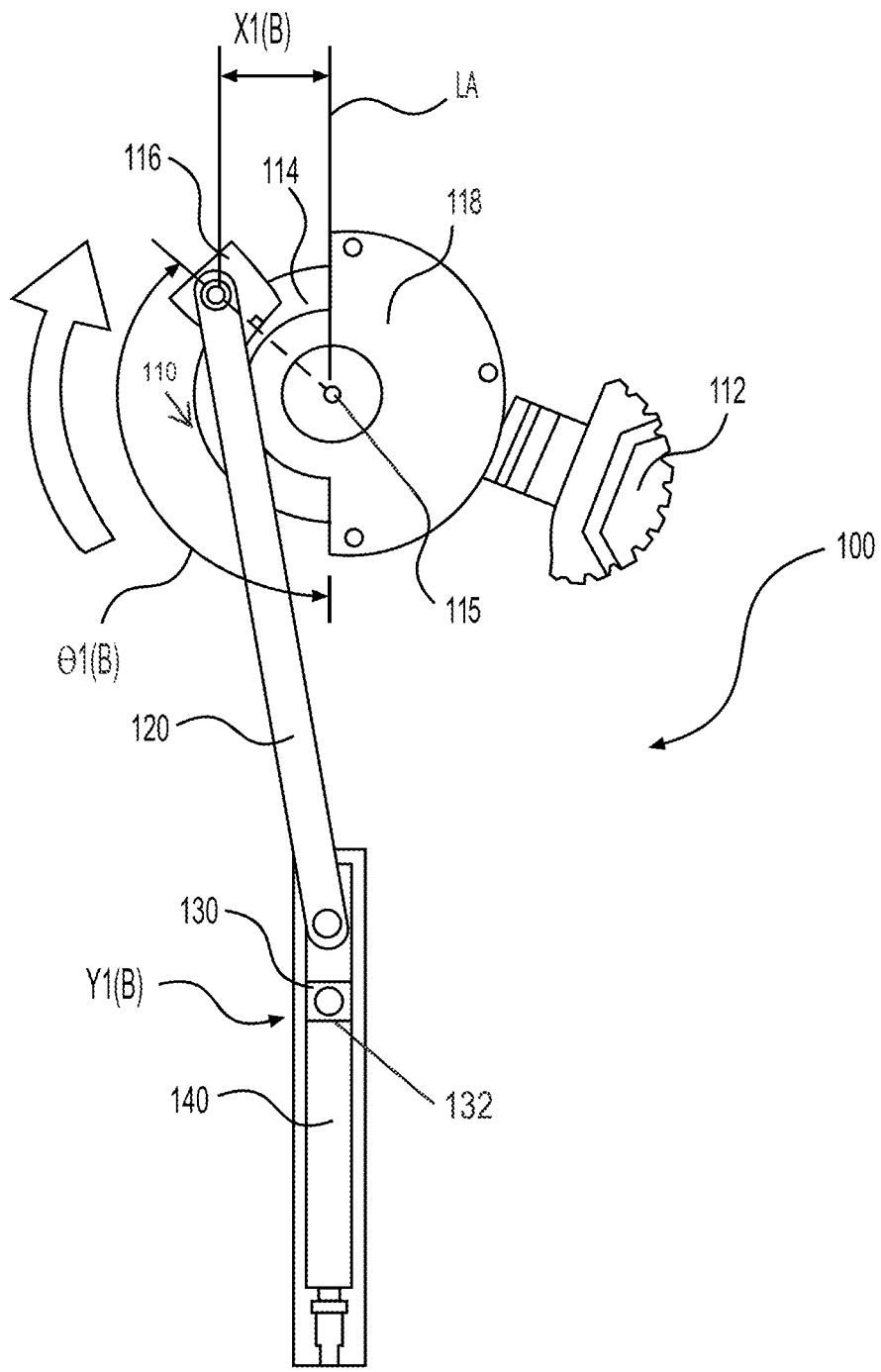

FIGS. 2A and 2B show an exemplary linkage assembly 100 in a first configuration (FIG. 2A) and a second configuration (FIG. 2B). The first configuration (FIG. 2A) may correspond to an elevator being in an initial, lowered (e.g., maximally, fully lowered) position. The second, final configuration (FIG. 2B) may correspond to an elevator being in a raised (e.g., maximally, fully raised) position.

Linkage assembly 100 may include a rotatable member 110, a connecting rod 120, and a plunger 130. Rotatable member 110 may include an elevator control lever 112, which may extend radially outward from an annular ring 114. Rotatable member 110 may be rotatable about a central axis 115 of annular ring 114. Annular ring 114 may be disposed within handle 12 (FIGS. 1A-1B), and elevator control lever 112 may extend outwardly through a housing of handle 12 via, e.g., a slit. Edges of the slit may define a range by which elevator control lever 112 may be moved. Alternatively, other structures internally to or externally of the housing of handle 12 (e.g., cover 118) may constrain a range by which elevator control lever 112 may be moved. Elevator control lever 112 may have a range extending from an initial position, at one end of a range of elevator control lever 112, to a final position, at the other end of a range of elevator control lever 112. Elevator control lever 112 may have any of the properties of elevator control lever 38 (FIG. 1B). Elevator control lever 112 may include ridges for providing a contact surface for a user's finger and may provide traction to a user.

Annular ring 114 may be rotatable relative to a housing of handle 12, such that movement of elevator control lever 112 causes rotation of annular ring 114 relative to the housing of handle 12. Annular ring 114 and elevator control lever 112 may be a single, unitary structure or may be attached to one another. A protrusion 116 may extend radially outward from annular ring 114. As shown, protrusion 116 may be a separate piece that is fixed to annular ring 114. Alternatively, protrusion 116 be formed integrally with annular ring 114 and/or control lever 112 or may be a separate piece.

Components of rotatable member 110 may be formed of any suitable material. For example, components of rotatable member 110 may be formed of rigid materials, such as plastic or other polymers, composites, or metal. Control lever 112, annular ring 114, and protrusion 116 may be formed from the same materials or from different materials.

As shown in FIGS. 2A and 2B, a cover 118 may cover at least a portion of annular ring 114. Cover 118 may provide for separation between annular ring 114 and other components of handle 12 and/or may be used to retain annular ring 114 within a desired plane. Cover 118 may be rotatable relative to rotatable member 110 (including annular ring 114). For example, cover 118 may be stationary relative to the housing of handle 12.

A proximal end of connecting rod 120 may be secured to protrusion 116 or to another portion of rotatable member 110. For example, a pin may secure connecting rod 120 to protrusion 116 such that connecting rod 120 is rotatable relative to protrusion 116. Connecting rod 120 may extend distally from rotatable member 110 within an interior of handle 12. As shown in FIGS. 2A and 2B, connecting rod 120 may be straight. Alternatively, connecting rod 120 may be curved and/or angled (see, e.g., FIGS. 4A and 4B). A distal end of connecting rod 120 may be rotatably coupled to plunger 130. For example, a pin or other structure may rotatably couple the distal end of connecting rod 120 to plunger 130. A proximal end of plunger 130 may be obscured in FIGS. 2A and 2B by the distal end of connecting rod 120. Connecting rod 120 may be formed of any suitable material. For example, connecting rod 120 may be formed of rigid materials, such as plastic or other polymers, composites, or metal. Control lever 112, annular ring 114, and protrusion 116 may be formed from the same materials or from different materials.

Plunger 130 may extend approximately parallel to the longitudinal axis of handle 12. A distal end 132 of plunger 130 may be coupled to a control wire (not shown), which may be coupled to the elevator. As the plunger moves proximally and distally, the control wire may be pulled proximally or pushed distally, respectively. This movement of the plunger and the control wire may cause the elevator to raise and/or lower. Plunger 130 may be formed of any suitable material. For example, plunger 130 may be formed of rigid materials, such as plastic or other polymers, composites, or metal.

A movement of plunger 130 may be constrained by a channel 140. Channel 140 may extend approximately parallel to the longitudinal axis of handle 12. Channel 140 may inhibit plunger 130 from moving in directions perpendicular to the longitudinal axis and may constrain plunger 130 to longitudinal movement. The control wire may pass through channel 140.

Various dimensions of linkage assembly 100 are noted in FIGS. 2A and 2B. L1 refers to a length of connecting rod 120 between its pivot points at the proximal and distal ends. As shown in FIGS. 2A and 2B, connecting rod L1 is the same in FIG. 2A and FIG. 2B, because connecting rod L1 may be rigid. θ1 may refer to an angle by which the proximal end of connecting rod 120 is rotated from a longitudinal axis LA, in for example, a clockwise direction (a direction of the arrow in FIGS. 2A and 2B). Longitudinal axis LA may extend through a rotational axis 115 of rotatable member 110. For example, longitudinal axis LA may be coaxial with a diameter of rotatable member 110. Longitudinal axis LA may be perpendicular to rotational axis 115. Longitudinal axis LA may be parallel with or coaxial to a central longitudinal axis of channel 140. Angles θ1(A) (FIG. 2A) and θ1(B) (FIG. 2B) may refer to the value of θ1 in the configurations of FIG. 2A (initial configuration with elevator lowered) and FIG. 2B (final configuration with elevator raised), respectively. θ1, θ1(A), and θ1(B) may each have a vertex at the intersection of axis 115 and longitudinal axis LA.

As shown in FIGS. 2A and 2B, longitudinal axis LA may be coaxial with the central longitudinal axis of channel 140. Alternatively, longitudinal axis LA may be offset from the central longitudinal axis of channel 140 (e.g., to the left or the right of the central longitudinal axis of channel 140 in FIGS. 2A and 2B. For example, channel 140 may be offset in a leftward direction of FIGS. 2A and 2B relative to longitudinal axis LA, such that channel 140 would intersect a path of a proximal end of connecting rod 120 at a value of θ1 between 90 degrees and θ1(B). Such a configuration may minimize a side-load for friction when elevator 116 is in a range of interest (e.g., above angles of 60 degrees). Longitudinal axis LA may additionally or alternatively be parallel to and/or coaxial with the longitudinal axis of handle 12, described above.

X1 denotes a distance from the proximal end of connecting rod 120 (at its pivot point) to the longitudinal axis LA of the handle 112, described above. X1(A) and X1(B) refer to the values of X1 in the configurations of FIG. 2A (initial configuration with elevator lowered) and 2B (final configuration with elevator raised), respectively. X1 may be equal to $R\sin(θ1)$.

In operation, an elevator may initially be in a lowered position (corresponding to the position of the linkage assembly shown in FIG. 2A). An angle of rotation of connecting rod 120 may have a value of θ1(A), which may correspond to a connecting rod lateral offset of X1(A). Plunger 130 may have a longitudinal position of Y1(A), corresponding to a lowered position of the elevator. The user may rotate elevator control lever 112, thereby rotating rotatable member 110 and moving a proximal end of connecting rod 120. In a final, raised position (corresponding to the position of the linkage assembly shown in FIG. 2B), an angle of rotation of connecting rod 120 may have a value of θ1(B), which may correspond to a connecting rod lateral offset of X1(B). Plunger 130 may have a longitudinal position of Y1(B), corresponding to a raised position of the elevator.

As rotatable member 110 rotates in the direction shown, the offset distance X1 changes. FIG. 5A is a graph depicting values of X1 for different values of θ1. The horizontal axis reflects the value of θ1. The vertical axis reflects the value of X1. X1 may have values between −1 and 1. This is because X1 has been normalized to show a sinusoidal curve. Actual values of X1 may vary and may reflect any suitable unit, while retaining the shape of the curve, described in detail below.

Were rotatable member 110 able to rotate a full 360 degrees, the value of X1 would vary in a sinusoidal pattern, between −1 and 1. But because a range of rotatable member 110 may be limited (as described above, for example, a range of control lever 112 may be limited by, e.g., edges of the housing of handle 12 or an edge of cover 118), only a portion of the sinusoidal curve may be traversed when elevator control lever 112 is operated, causing rotatable member 110 to rotate. The solid curve 410 of FIG. 5A reflects how lateral offset X1 varies over the typical usable range. The dotted curve of FIG. 5A shows the portions of the sinusoidal curve that are not captured by movement of control lever 112/rotatable member 110 due to limitations on the range of rotatable member 110 (or other portions of linkage assembly 100).

θ1(A) may be approximately 45 degrees and may reflect the value of θ1 when the elevator is in an initial, lowered position. The left-most end of solid curve 410 may reflect the value of θ1(A). θ1(B) may be approximately 135 degrees and may reflect the value of θ1 when the elevator is in a raised position. The right-most end of solid curve 410 may reflect the value of θ1(B). Rotatable member 110 (including control lever 112) may thus be rotatable by approximately 90 degrees. The angular values provided above are merely exemplary. For example, a range of rotatable member 110 may be more or less than 90 degrees.

With reference to FIG. 5A, as control lever 112 is rotated clockwise, as shown by the arrow of FIG. 2A, and the value of θ1 increases, the value of X1 first increases, until θ1 is approximately 90 degrees. As rotatable member 110 continues to rotate, the value of X1 then decreases. Because the range of values of δ1 may be approximately centered about 90 degrees, the values of X1 during the rotation of rotatable member 110 may be the top portion of the sinusoidal curve described above.

The mechanical advantage of linkage assembly 100 is graphed in FIG. 5B. The mechanical advantage may be a ratio of a force produced by linkage assembly 100 to a force applied to linkage assembly 100. A higher mechanical advantage indicates a greater multiplier/magnification of the force applied to elevator control lever 112. When the mechanical advantage is higher, less force is required on connecting rod in order to achieve the same motion of the elevator.

FIG. 5B shows, in a dashed curve 420, the mechanical advantage of linkage assembly 100 over the path of travel of rotatable member 110. The dashed curve 420 of FIG. 5B may cover the same range of rotation as the solid line (X1 value) in FIG. 5A. As shown in FIG. 5B, the mechanical advantage (dashed curve 420) is inversely proportional to the value of X1 (solid curve 410). Mechanical advantage may be inversely proportional to a lever length (e.g., X1). A mechanical advantage of linkage assembly 100 may be equal to an inversion of the lever length (1/X1). X1 may be equal to a distance from rotational axis 115 to a proximal end of connecting rod 120 (which may be approximately the same as a radius of rotatable member 110) and may be equal to $1/(R\sinθ1)$. As with the graph of values of X1 (the solid curve 410 of FIG. 5A), the graph of values of mechanical advantage (the dashed curve 420 of FIG. 5B) may be approximately symmetrical. The mechanical advantage is approximately 1.4 at θ1(A) (the initial, lowered position of the elevator) and θ1(B) (the final, raised position of the elevator). As rotatable member 110 rotates, and the elevator is raised, the mechanical advantage first decreases to a value of approximately 1 before then increasing again. The mechanical advantage (FIG. 5B) is at a minimum where X1 (FIG. 5A) is at a maximum, which is at the value θ1=90°.

As discussed above, as the elevator is raised, the amount of force required to raise the elevator increases. The configuration of rotatable member 110 provides a relatively modest level of mechanical advantage throughout the range of the elevator, including as the elevator is raised to the area of interest (where the operator may desire to fine tune positioning).

Figure 3A:
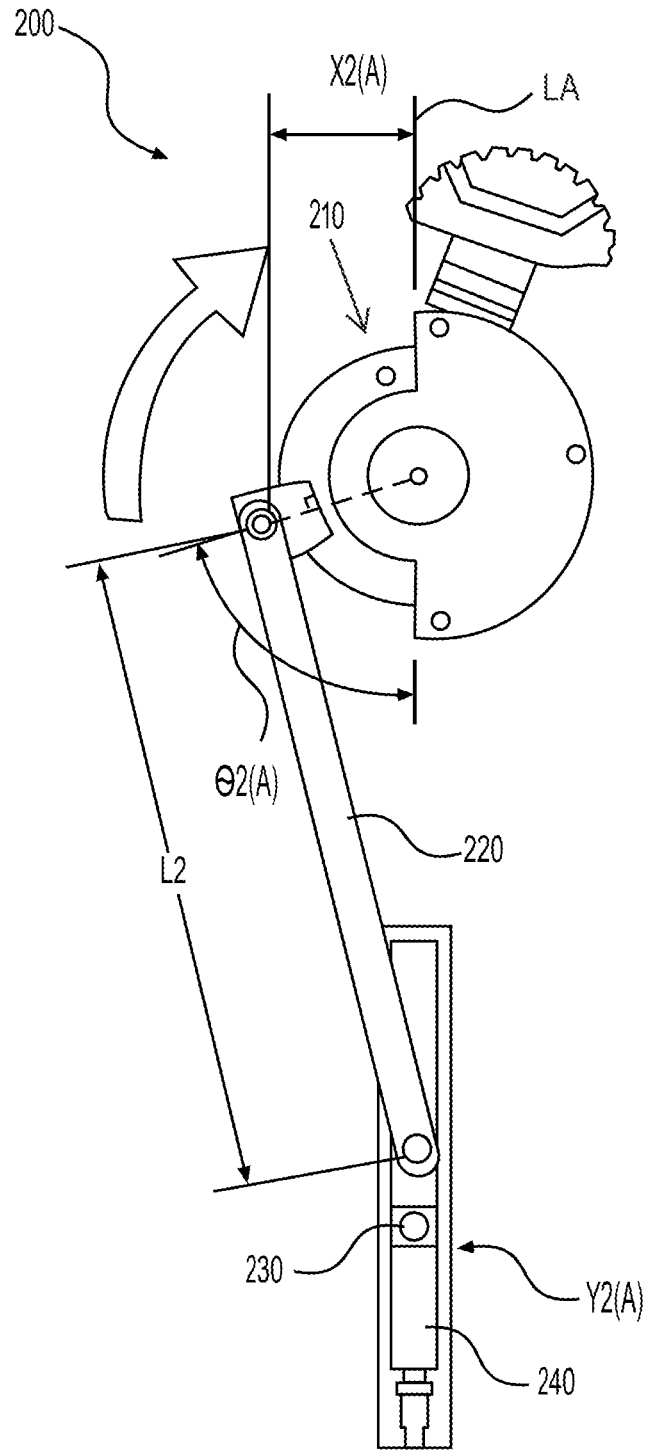
Figure 3B:
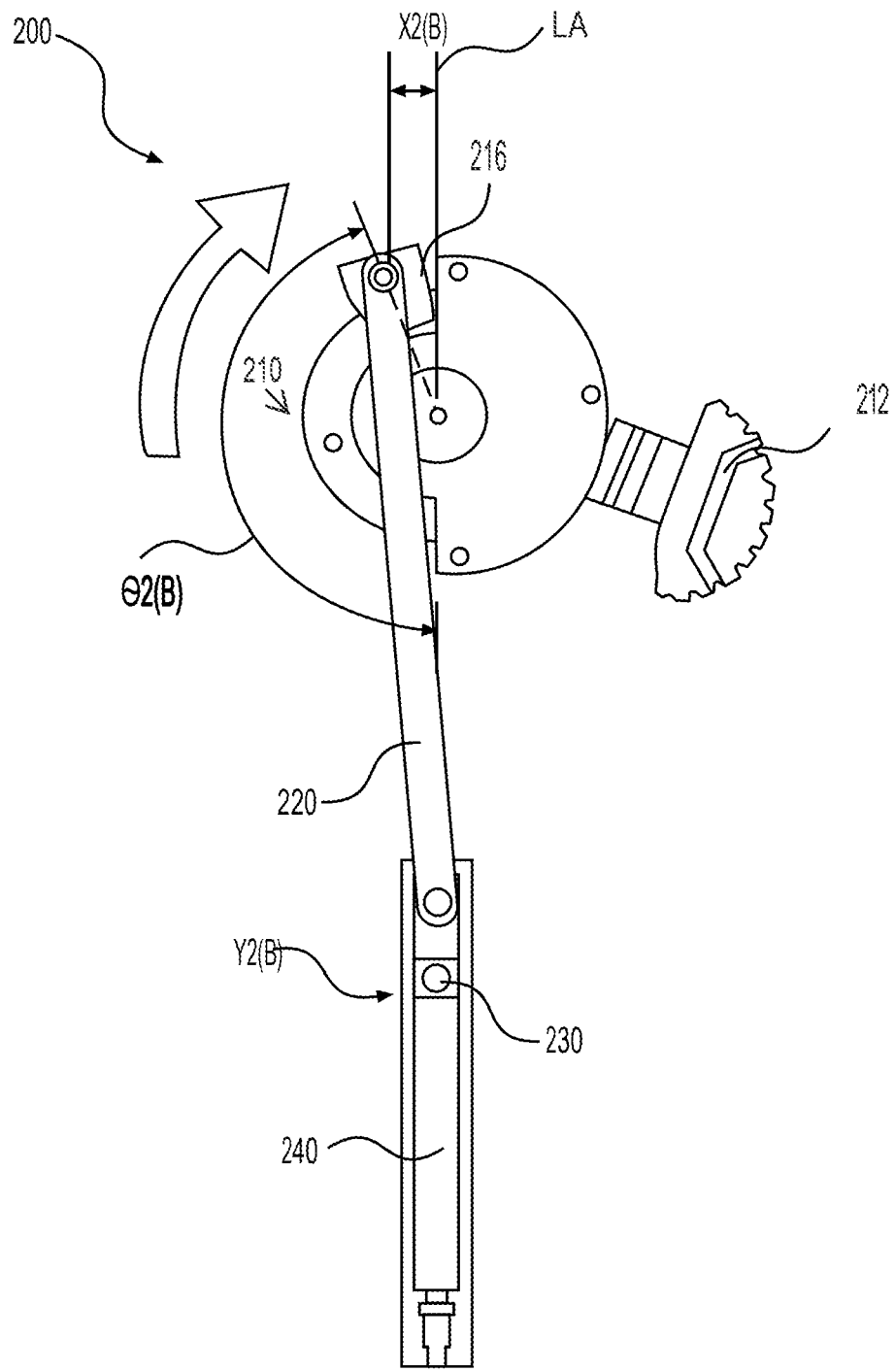

FIGS. 3A and 3B depict an alternative linkage assembly 200. Linkage assembly 200 may have any of the properties of linkage assembly 100, except as where specified below. As compared with linkage assembly 100, linkage assembly 200 may provide a greater mechanical advantages at greater angles of the elevator while maintaining the same change in angle of the elevator. This increased mechanical advantage may require less force to be exerted to raise the elevator as compared with linkage assembly 100. In particular, linkage assembly 200 may facilitate fine steering of the elevator at higher levels of elevation of the elevator. Furthermore, a velocity of movement of the elevator at higher angles may be smaller with linkage assembly 200 than with linkage assembly 100. The decreased velocity may further facilitate precise, fine-tuned steering.

FIGS. 3A and 3B show linkage assembly 200 in a first configuration (FIG. 3A) and a second configuration (FIG. 3B). The first configuration (FIG. 3A) may correspond to an elevator being in a lowered (e.g., fully/maximally lowered) position. The second configuration (FIG. 3B) may correspond to an elevator being in a raised (e.g., fully/maximally raised) position.

Linkage assembly 200 may include a rotatable member 210, a connecting rod 220, and a plunger 230. Rotatable member 210, connecting rod 220, and plunger 230 may have any of the properties of rotatable member 110, connecting rod 120, and plunger 130, respectively, except as where specified herein. Rotatable member 210 may include an elevator control lever 212, which may have any of the properties of elevator control lever 112. A length L2 of connecting rod 220 may be the same as the length L1 of connecting rod 120, or the lengths may be different. Plunger 230 may ride along channel 240, which may have any of the properties of channel 140.

As compared with rotatable member 110 and connecting rod 120, connecting rod 220 may be coupled to rotatable member 210 at a different location. Compared to protrusion 116 of rotatable member 110, protrusion 216 may have an alternative positioning on rotatable member 210. An angle in the clockwise direction from control lever 212 to protrusion 216/the attachment location of connecting rod 220 may be smaller than an angle in the clockwise direction from control lever 112 to protrusion 116/the attachment location of connecting rod 120. In other words, an angular offset θ2(A) of the proximal end of connecting rod 220 from longitudinal axis LA (described above with respect to FIGS. 2A-2B), in the lowered configuration of the elevator, may be greater than angular offset θ1(A) of connecting rod 120. And an angular offset θ2(B) of the proximal end of connecting rod 220 from the longitudinal axis LA (described above), in the raised configuration of the elevator, may be greater than angular offset θ1(B) of connecting rod 120. θ2, θ2(A), and θ2(B) may each have a vertex at the intersection of axis 115 (described above) and longitudinal axis LA In operation, an elevator may initially be in a lowered position (corresponding to the position of linkage assembly 200 shown in FIG. 3A). An angle of rotation of connecting rod 320 may have a value of θ2(A), which may correspond to a connecting rod lateral offset of X2(A). Plunger 230 may have a longitudinal position of Y2(A), corresponding to a lowered position of the elevator. The user may rotate elevator control lever 212, thereby rotating rotatable member 210 and moving a proximal end of connecting rod 220. In a raised position (corresponding to the position of linkage assembly 200 shown in FIG. 3B, an angle of rotation of connecting rod 220 may have a value of θ2(B), which may correspond to a connecting rod lateral offset of X2(B). Plunger 230 may have a longitudinal position of Y2(B), corresponding to a raised position of the elevator.

In the lowered position of the elevator (FIGS. 2A, 3A), an offset X2(A) of connecting rod 220 may be greater than an offset X1(A) of connecting rod 120, and an angular offset θ2(A) of connecting rod 220 from longitudinal axis LA of may be greater than angular offset θ1(A) of connecting rod 120. In the raised position of the elevator (FIGS. 2B, 3B), an offset X2(B) of connecting rod 220 may be smaller than an offset X1(B) of connecting rod 120, and an angular offset θ2(B) of connecting rod 220 from longitudinal axis LA of may be greater than angular offset θ1(B) of connecting rod 120.

FIG. 6A shows a graph reflecting changes in the values of θ2 and X2. The horizontal axis reflects the value of θ2. The vertical axis reflects a value of X2. X2 may have values between −1 and 1. This is because X2 has been normalized to show a sinusoidal curve. Actual values of X2 may vary and may reflect any suitable unit. Even if the values of X2 are different, a shape of a curve 510 (described in further detail below) may remain the same.

Were rotatable member 210 able to rotate a full 360 degrees, the value of X2 may vary in a sinusoidal pattern, between −1 and 1. But because a range of rotatable member 210 may be limited (as described above, for example, a range of control lever 212 may be limited by, e.g., edges of the housing of handle 12 or edges of cover 118, as described with respect to FIGS. 2A and 2B), only a portion of the sinusoidal curve may be traversed during movement of rotatable member 210. The solid curve 510 of FIG. 6A reflects how lateral offset X2 varies over the usable range. The dotted curve of FIG. 6A shows the portions of the sinusoidal curve that are not captured due to limitations on the range of rotatable member 210 (or other portions of linkage assembly 200).

θ2(A) may be approximately 70 degrees and may reflect the value of θ2 when the elevator is in a lowered position. The left-most end of solid curve 510 may reflect the value of θ2(A). θ2(B) may be approximately 160 degrees and may reflect the value of θ2 when the elevator is in a raised position. The right-most end of solid curve 510 may reflect the value of θ2(B). Rotatable member 210 (including control lever 212) may thus be rotatable by approximately 90 degrees. The angular values provided above are merely exemplary. For example, a range of rotatable member 210 may be more or less than 90 degrees.

As compared with solid curve 410 of values of X1 (FIG. 5A), it will be appreciated that solid curve 510 of values of X2 (FIG. 6A) is horizontally shifted to the right by an amount equal to the difference between θ2(A) and θ1(A). In other words, the portion of the sinusoidal curve (solid curve 510) captured by motion of rotatable member 210 is shifted to the right relative to the portion of the sinusoidal curve (solid curve 410) captured by motion of rotatable member 110. The values of X1 (FIG. 5A, relating to linkage assembly 100) correspond the top portion of the sinusoidal curve, approximately symmetrically. In contrast, the values of X2 (FIG. 5B, relating to linkage assembly 200) are asymmetrical.

As control lever 212 is actuated, rotating rotatable member 210 clockwise (as shown by the arrow in FIGS. 3A and 3B), X2 varies as shown by solid line 510 in FIG. 6A. In the initial stages (when the elevator is at lower angles), X2 increases slightly along the sinusoidal curve before peaking (e.g., at a value of θ2 of 90 degrees). X2 then decreases along the sinusoidal curve. As discussed above, the graph of values of X2 (solid curve 510 of FIG. 6A) is asymmetrical such that the portion of solid curve 510 to the right of the peak of solid curve 510 is larger than the portion of solid curve 510 to the left of the peak of solid curve 510. For example, the portion of solid curve 510 to the left of the peak (at an angle of rotation θ2 of 90 degrees) may be approximately 15%-30% of the total curve.

As shown in FIG. 6A, a value of X2 (e.g., X2(A)) at a start of the stroke of linkage system 200 may be slightly less than 1 (e.g., approximately 0.8 to approximately 1.0 or, more specifically, approximately 0.85 to approximately 0.95) on the scale of FIG. 6A. A value of X2 (e.g. X2(B)) at an end of the stroke of linkage system 200 may be less than 0.5 (e.g., approximately 0.25 to approximately 0.5, or approximately 0.30 to approximately 0.40).

The mechanical advantage of linkage assembly 200 is graphed in FIG. 6B. The mechanical advantage may be a ratio of a force produced by linkage assembly 200 to a force applied to linkage assembly 200. A higher mechanical advantage indicates a greater multiplier/magnification of the force applied to lever 212. When the mechanical advantage is higher, less force is required on connecting rod in order to achieve the same motion of the elevator were the mechanical advantage lower.

FIG. 6B shows, in a dashed curve 520, the mechanical advantage of linkage assembly 200 over the path of travel of rotatable member 210. Dashed curve 520 of FIG. 6B may cover the same range of rotation as solid line 510 (X2 value) in FIG. 6A. As shown in FIG. 6B, and as discussed above with respect to FIG. 6A, the mechanical advantage (dashed curve 520) is inversely proportional to the value of X2.

The mechanical advantage is just greater than 1 (e.g., approximately 1.0-1.1) at θ2(A) (the lowered position of the elevator). The mechanical advantage is approximately 3 at θ2(B) (the raised position of the elevator). As rotatable member 210 rotates, and the elevator is raised, the mechanical advantage first decreases slightly to a value of approximately 1 before then increasing again. The mechanical advantage (FIG. 6B) is at a minimum where X2 (FIG. 6A) is at a maximum, which is at the value of θ2=90° (i.e., θ2(B)).

As discussed above, as the elevator is raised, the amount of force required to raise the elevator increases. The configuration of linkage assembly 200 produces increasing mechanical advantage as the elevator is raised to higher levels. The mechanical advantage counteracts or at least partially counteracts the increased force required to raise the elevator at higher angles. For example, values of θ2 between approximately 140 degrees and approximately 160 degrees (e.g., between 145 degrees and approximately 155 degrees) may correspond to a range of elevator incline that is of particular interest to an operator. This angular range corresponds to mechanical advantages of approximately 1.56 to approximately 2.92 (e.g., approximately 1.74 to approximately 2.36).

At a beginning of the stroke of linkage assembly 200 (the configuration of FIG. 3A), a mechanical advantage of linkage assembly 200 may be slightly greater than 1 (e.g. between approximately 1.0 and approximately 1.5, or more specifically between 1.01 and 1.15). At an end of the stroke of linkage assembly 200 (the configuration of FIG. 3B), the mechanical advantage of linkage assembly 200 may be approximately 3, such that the mechanical advantage increases by approximately 300 percent over the course of the stroke. The mechanical advantage of linkage assembly 200 at the end of the stroke may alternatively be higher or lower (e.g., may be at least approximately 1.5, at most approximately 10, or some other value).

As shown in FIG. 6B, and as shown above, a mechanical advantage at an end of the stroke (FIG. 3B) of linkage assembly 200 may be at least 50 percent higher than a mechanical advantage at a beginning of the stroke (FIG. 3A). Alternatively, the mechanical advantage at an end of the stroke (FIG. 3B) of linkage assembly 200 may be at least 175 percent or 300 percent higher than the mechanical advantage at a beginning of the stroke (FIG. 3A). Such a relationship between the mechanical advantage at the beginning of the stroke and the mechanical advantage at the end of the stroke may facilitate raising the elevator to higher deflection levels using less force, and may facilitate fine steering of the elevator at deflection levels of interest. An at least 50% increase in mechanical advantage may correspond to a linkage assembly in which an offset value of connecting rod 220 at the end of the stroke (e.g., X2(B)) is less than two-thirds of the offset value of connecting rod 220 at the beginning of the stroke (e.g., X2(A)). When X2(B) is two-thirds of X2(A), a mechanical advantage (inverse of the two-thirds value) may be 150%. For example, as shown in FIG. 6A, X2(B) is approximately half of X2(A).

As compared with, for example, linkage assembly 100, linkage assembly 200 requires much less force to raise the elevator at higher angles. The decrease in force facilitates a user's ability to fine tune the elevator angle in order to precisely position a medical device passed down the working channel. Furthermore, the configuration of linkage assembly 200 results in higher velocity movement of the elevator at lower angles and lower velocity movement of the elevator at higher angles. A user is able to quickly move the elevator to the lower end of the range of interest and then more easily fine tune positioning at an angle of interest, aided by the decreased velocity.

Figure 4A:
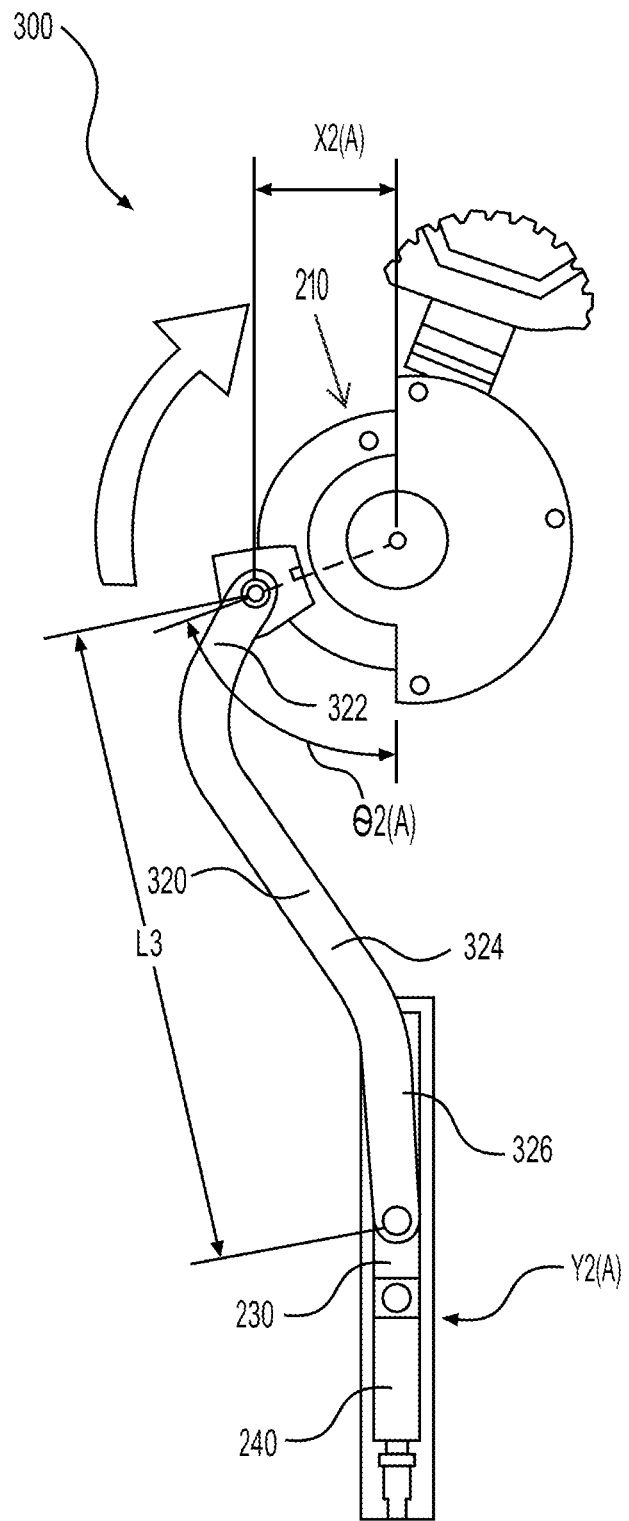
Figure 4B:
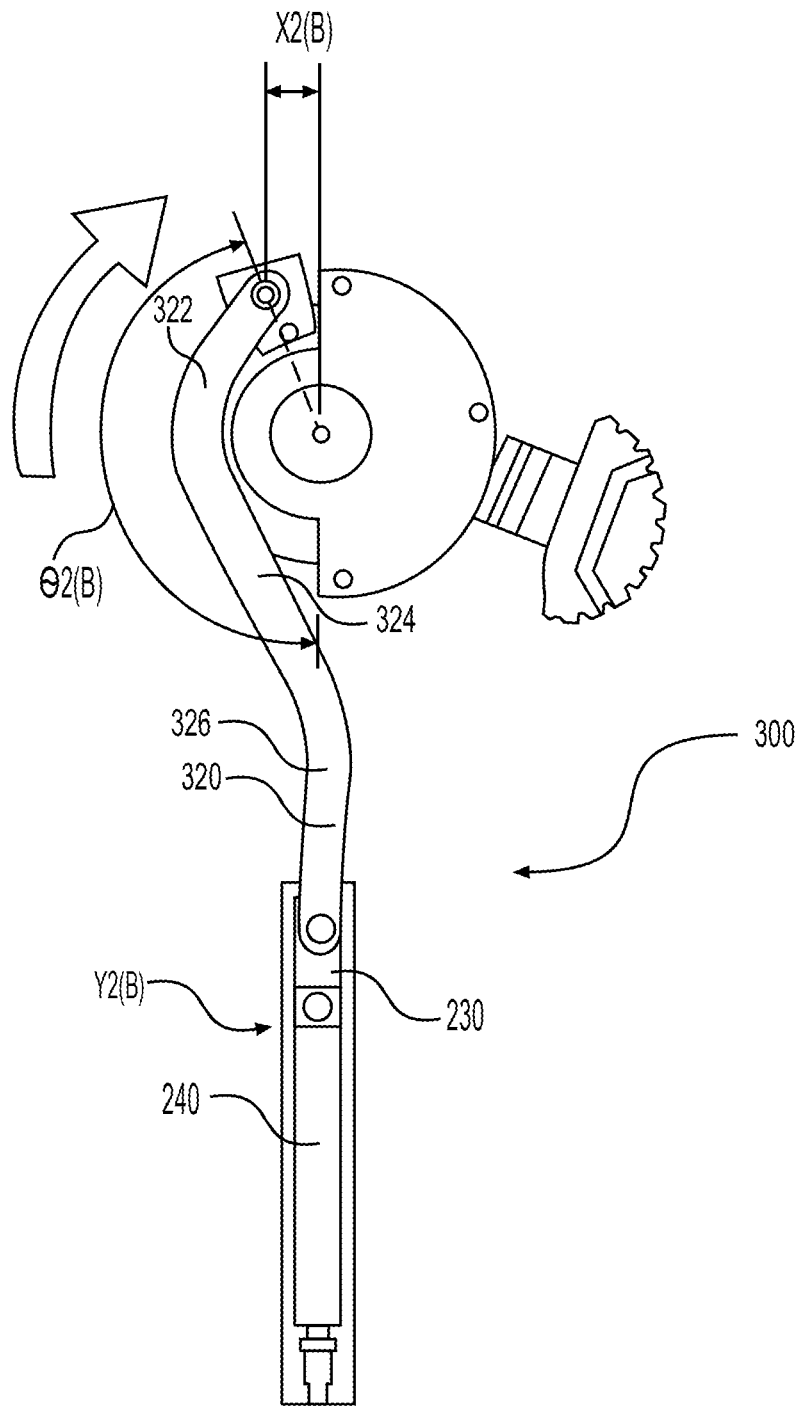

FIGS. 4A and 4B depict another example linkage assembly 300. In FIG. 4A, linkage assembly 300 is in a lowered configuration (e.g., a fully/maximally lowered configuration). In FIG. 4B, linkage assembly 300 is in a raised (e.g., a fully/maximally raised) configuration. Linkage assembly 300 may have any of the properties of linkage assembly 100 or, in particular, linkage assembly 200. Linkage assembly 300 may have the same properties of linkage assembly 200, except where as specified below.

Linkage assembly 320 may have a connecting rod 320. Connecting rod 320 may differ from connecting rod 220 in that connecting rod 320 has an angled (non-linear) shape, described below. Although connecting rod 320 has a different shape from connecting rod 220, connecting rod has the same length as connecting rod 220, such that L3=L2. Connecting rod 320 may also be coupled to rotatable member 210 at the same position as connecting rod 220 is coupled to rotatable member 210. Therefore, the graphs of FIGS. 6A-6B apply equally to linkage assembly 300 as they do to linkage assembly 200, and linkage assembly 300 has the advantages of linkage assembly 200 with respect to mechanical advantage and other properties.

Connecting rod 320 may follow a zigzag (non-linear) pattern or geometry. Connecting rod 320 may include three or more segments, 322, 324, and 326, each of which may be transverse to one another. Segment 324 may be disposed between segments 322 and 324. An interior angle between segments 322 and 324 may be smaller or larger than an interior angle between segments 324 and 326. Both of the interior angles may be obtuse. Segments 322 and 326 may have approximately the same length. Segment 324 may be longer or shorter than either of segments 322 and 326. As shown by FIG. 4A, segments 322, 324, and 326 may be joined at rounded joints.

A shape of connecting rod 320 may be chosen to avoid interference with other components of handle 12. Connecting rod 320 may move freely upon actuation of elevator control lever 212, without disturbing other components of handle 12 or being disturbed by the other components. A shape of connecting rod 320 shown in FIGS. 4A and 4B is merely exemplary. Any suitable shape may be chosen in order to avoid interference between connecting rod 320 and other components of the handle.

While principles of this disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A linkage assembly for a medical device, the linkage assembly comprising:
   a rotatable member configured to rotate about a rotation axis;
   a plunger; and
   a connecting rod rotatably connected to the rotatable member and the plunger and movable along a range, wherein a first end of the range corresponds to an initial position of a distal member movable by the linkage assembly, and a second end of the range corresponds to a final position of the distal member,
   wherein the connecting rod consists of a first segment, a second segment, and a third segment, wherein the second segment is disposed between the first segment and the third segment, wherein the first segment is movably coupled to the rotatable member, wherein the third segment is movable coupled to the plunger, wherein each of the first segment and the third segment are angled relative to the second segment,
   wherein a first angle between the first segment and the second segment on a first side of the connecting rod is less than a second angle between the second segment and the third segment on the first side of the connecting rod,
   wherein, in a first configuration of the linkage assembly, at the first end of the range, a proximal end of the connecting rod is offset from a longitudinal axis by a first distance, wherein the longitudinal axis is perpendicular to the rotation axis, wherein, in the first configuration, a proximal end of the connecting rod is offset from the longitudinal axis of the linkage assembly by approximately 70 degrees, and wherein the second segment is transverse to the longitudinal axis;
   wherein, in a second configuration of the linkage assembly, at the second end of the range, the proximal end of the connecting rod is offset from the longitudinal axis by a second distance, wherein the second distance is less than two-thirds of the first distance, wherein the proximal end of the connecting rod is offset from the longitudinal axis of the linkage assembly by approximately 160 degrees, and wherein the second segment is transverse to the longitudinal axis.

2. The linkage assembly of claim 1, wherein a mechanical advantage of the linkage assembly is at least 175 percent higher in the second configuration than in the first configuration.

3. The linkage assembly of claim 1, wherein the first configuration is at a starting point of a stroke of the linkage assembly.

4. The linkage assembly of claim 3, wherein the second configuration is at an ending point of the stroke of the linkage assembly.

5. The linkage assembly of claim 1, wherein the rotatable member is rotatable by a lever fixed to the rotatable member.

6. The linkage assembly of claim 1, wherein the plunger is operative to move a control wire coupled to the distal member.

7. The linkage assembly of claim 1, wherein the distal member is an elevator of the medical device.

8. The linkage assembly of claim 7, wherein, in the first configuration, the elevator is in a fully lowered configuration, and wherein, in the second configuration, the elevator is in a fully raised configuration.

9. The linkage assembly of claim 1, wherein the longitudinal axis is coaxial with a diameter of the rotatable member that extends through the rotation axis.

10. The linkage assembly of claim 1, wherein the longitudinal axis of the linkage assembly defines a longitudinal movement of the plunger.

11. The linkage assembly of claim 5, wherein in the first configuration, the proximal end of the lever is offset, in a first direction, from the longitudinal axis by a fifth angle, wherein, in the second configuration, the proximal end of the lever is offset, in the first direction, from the longitudinal axis by a sixth angle, and wherein the sixth angle is larger than the fifth angle, and wherein the fifth angle and the sixth angle each has a vertex at an intersection of the rotation axis of the rotatable member and the longitudinal axis of the linkage assembly.

12. The linkage assembly of claim 11, wherein a first leg of each of the fifth angle and the sixth angle is defined by a line extending between the rotation axis and the proximal end of the lever, and wherein a second leg of each of the fifth angle and the sixth angle is defined by the longitudinal axis of the linkage assembly.

13. A linkage assembly for a medical device, the linkage assembly comprising:
   a rotatable member configured to rotate about a rotational axis;
   a plunger; and
   a connecting rod rotatably connected to the rotatable member and the plunger and movable along a range, wherein a first end of the range corresponds to an initial position of a distal member movable by the linkage assembly, and a second end of the range corresponds to a final position of a distal member;
   wherein in a first configuration of the connecting rod, at a first end of the range, the linkage assembly has a first mechanical advantage, wherein, in a second configuration of the connecting rod, at a second end of the range, the linkage assembly has a second mechanical advantage, wherein the second mechanical advantage is at least 175 percent higher than the first mechanical advantage; and wherein a longitudinal axis of the linkage assembly extends perpendicularly through the rotational axis of the rotatable member and is coaxial to a longitudinal axis of the plunger, wherein the connecting rod consists of a first segment, a second segment, and a third segment, wherein the second segment is disposed between the first segment and the third segment, wherein each of the first segment and the third segment are angled relative to the second segment, wherein a first angle between the first segment and the second segment on a first side of the connecting rod is less than a second angle between the second segment and the third segment on the first side of the connecting rod, wherein, in the first configuration, a proximal end of the connecting rod is offset from the longitudinal axis of the linkage assembly by approximately 70 degrees, and wherein the second segment is transverse to the longitudinal axis, wherein, in the second configuration, the proximal end of the connecting rod is offset from the longitudinal axis of the linkage assembly by approximately 160 degrees, and wherein the second segment is transverse to the longitudinal axis.

14. The linkage assembly of claim 13, wherein the rotatable member is rotatable by a lever fixed to the rotatable member, wherein in the first configuration, a proximal end of the lever is offset, in a first direction, from a longitudinal axis of the linkage assembly by a first angle, wherein, in the second configuration, the proximal end of the lever is offset, in the first direction, from the longitudinal axis by a second angle, and wherein the second angle is larger than the first angle, and wherein the first angle and the second angle each has a vertex at an intersection of the rotational axis of the rotatable member and the longitudinal axis of the linkage assembly.

15. The linkage assembly of claim 13, wherein the distal member is an elevator of the medical device.

16. The linkage assembly of claim 15, wherein, in the first configuration, the elevator has a lower deflection angle than in the second configuration.

17. A linkage assembly for a medical device, the linkage assembly comprising:
a connecting rod connected to a rotatable member and a plunger, wherein the connecting rod is nonlinear, wherein the rotatable member is configured to rotate about a rotation axis along a range, wherein a first end of the range corresponds to an initial position of a distal member movable by the linkage assembly, and a second end of the range corresponds to a final position of the distal member, wherein, in a first configuration of the connecting rod, in which the connecting rod is positioned at the first end of the range, a proximal end of the connecting rod is offset from a longitudinal axis of the linkage assembly by approximately 70 degrees, wherein the longitudinal axis is perpendicular to the rotation axis and extends through the rotation axis of the rotatable member and the plunger, wherein at the first end of the range, the plunger is in a distalmost position relative to the rotatable member, wherein in a second configuration of the linkage assembly, in which the connecting rod is positioned at the second end of the range, the proximal end of the connecting rod is offset from the longitudinal axis of the linkage assembly by approximately 160 degrees, wherein at the second end of the range, the plunger is in a proximalmost position relative to the rotatable member, and wherein a mechanical advantage of the linkage assembly is at least 50% higher in the second configuration than in the first configuration.

18. The linkage assembly of claim 17, wherein the mechanical advantage of the linkage assembly is at least 300% higher in the second configuration than in the first configuration.

19. The linkage assembly of claim 13, wherein the second mechanical advantage of the linkage assembly is at least 300% higher than the first mechanical advantage.

20. The linkage assembly of claim 1, wherein a mechanical advantage of the linkage assembly is at least 300% higher in the second configuration than in the first configuration.

* * * * *